United States Patent

Stäger et al.

[11] Patent Number: 5,923,037
[45] Date of Patent: Jul. 13, 1999

[54] DEVICE FOR DETERMINING THE OZONE CONCENTRATION IN AIR

[75] Inventors: Rainer Stäger, Munich; Gerd Uhlemann, Germering; Reinhold Busen, Greifenberg; Hans Güsten, Speyer, all of Germany; Anthony Delany, Eldorado Springs, Colo.

[73] Assignee: Deutsche Forschungsanstalt fur Luft-und Raumfahrt E.V., Köln, Germany

[21] Appl. No.: 08/971,579

[22] Filed: Nov. 17, 1997

[30] Foreign Application Priority Data

Nov. 15, 1996 [DE] Germany .................. 196 47 185

[51] Int. Cl.⁶ .................................................. G01N 21/76
[52] U.S. Cl. .................. 250/361 C; 250/361 R; 422/52
[58] Field of Search .................. 250/361 C, 361 R, 250/252.1 A; 422/52

[56] References Cited

U.S. PATENT DOCUMENTS 4,822,564  4/1989  Howard ....................................... 422/52

FOREIGN PATENT DOCUMENTS 213997   9/1984  German Dem. Rep. .
2208561  8/1990  Japan ..................................... 250/361

OTHER PUBLICATIONS

S. Sahand et al., "A batter–powered light–weight ozone analyzer for use in the troposhere and stratosphere", 1987.
U. Schurath et al., "Principle and application of a fast sensor for atmospheric ozone", Fresenius J Anal Chem, vol. 340, pp. 544–547, 1991.
H. Gusten et al., "Ein neuartiger Ozonsensor fur vielfaltige Anwendungen in der Umwelt", PTB–Mitteilungen 103 pp. 324–328, 1993.

Primary Examiner—Edward P. Westin
Assistant Examiner—Richard Hanig
Attorney, Agent, or Firm—Browdy and Neimark

[57] ABSTRACT

In a device for determining the ozone concentration by utilizing the surface chemiluminescence effect having a fan (13), a chemiluminescence element (8), a photomultiplier (6), a temperature sensor (16), and control electronics (12), an airflow generated by a fan (13) passes via a suction pipe (7) and an adjoining light trap system (17) through a venturi-shaped channel structure (2) along a metal block (9) in which a temperature sensor (16) is housed. The device is calibrated with respect to the temperature dependence of the reaction of a chemiluminescence disc (8) attached to the bottom of the metal block by determining the output voltage of a photomultiplier (6) in dependence on the temperature at a predetermined ozone concentration in the measured air. Also integrated into the metal block (9) is a light-emitting diode (LED 15) which is switched in a predetermined switching cycle as a reference light intensity and sends a light to the photomultiplier (6) via an opening (3) in the metal block (9), thus periodically overriding the actual ozone measurement process and resulting in a periodic calibration of the temperature dependence of the output voltage of the photomultiplier (6).

20 Claims, 4 Drawing Sheets

DEVICE FOR DETERMINING THE OZONE CONCENTRATION IN AIR

FIELD OF THE INVENTION

This invention relates to a device for determining the ozone concentration in air by utilizing the surface chemiluminescence effect.

REVIEW OF THE RELATED TECHNOLOGY

In climate research and during routine weather observations it is frequently necessary to measure vertical ozone profiles in the atmosphere. Over easily accessible areas such measurements are generally performed from the ground with balloon sondes. Over areas with difficult access, such as deserts, oceans and polar regions, it is usually impractical or impossible to measure vertical ozone profiles with balloon sondes and the measurements are therefore usually carried out from an aircraft.

In these cases the measurements are taken from the aircraft by means of LIDAR methods or other ozone sensors. LIDAR methods are complex, not always available, and their applicability is limited by clouds. Other types of ozone sensors used in aircraft require complex flying maneuvers to measure vertical ozone profiles.

An efficient alternative are dropsondes which can be launched from the aircraft and contain a suitable ozone sensor. Dropsondes of this type have been developed by the DLR (Deutsche Forschungsanstalt fuer Luft- und Raumfahrt e.V. (German Aerospace Research Center), Linder Hoehe 51147 Koeln, Germany) and the National Center of Atmospheric Research (NCAR) in Boulder, Colo., USA.

The dropsondes are launched from research aircraft flying at high altitudes. Several seconds after the launch, a parachute on the sonde opens and the sonde glides to the earth. During its flight the dropsonde continually measures meteorological data and transmits the measured values to the aircraft.

The applicant is not aware of any ozone sensors that are specifically used as dropsonde sensors launched from aircraft. There are, however, ozone sensors that take off in balloon sondes (radiosondes) from the ground. There are also ozone sensors that are launched into the atmosphere from the ground with rockets.

These ozone sensors have the following drawbacks regarding their use in dropsondes which can be launched from aircraft.

To date, the ozone-sensing element most frequently used in radiosondes is an electrochemical cell. With this technology the measurement air is transported, with the aid of a motor-driven piston, to the bottom of the electrochemical cell where it enters, in the form of small bubbles, into a potassium iodide solution. The ozone present in the measurement air causes an oxidation of the iodide anions present in the solution. The resulting electron flow between the electrodes of the electrochemical cell then becomes a measure for the ozone concentration.

The use of this technology in dropsondes essentially poses the following technical problems. On one hand, there is a risk that the liquid electrolyte may leak, because of the uncontrolled movements performed by the dropsonde during the time between its launch and the complete opening of the parachute. Preventing this would require either a position stabilizer or leak protection which, however, would be difficult to implement since the system must remain open for the measurement air to enter.

On the other hand, a significant drawback to the use of electrochemical cells in a dropsonde lies in the slow response to changes in ozone concentrations ranging from 20 sec to 1 min. At an average velocity of 20 meters per second (m/s) a dropsonde falls 400 m to 1.2 kilometers (km), resulting in a proportionate smoothing of the ozone profile.

The so-called light absorption technology utilizes the dependence of the absorption of ultraviolet light on the ozone mixing ratio in the measured air. It has been found, however, that the existing systems have the following drawbacks regarding their application as ozone sensors in dropsondes. To attain a sufficient absorption at low pressures, the absorption path must have a certain minimum length. This, in turn, however, results in dimensions for which there is insufficient room inside a small dropsonde. Furthermore, the known W absorption sensors weigh too much to be used in dropsondes and they are also too expensive to have a meaningful application in a kind of "disposable product", such as a dropsonde.

Surface chemiluminescence technology uses color-coated silica gel discs, sometimes also referred to as "target". The reaction between these discs and the ozone molecules in the measured air causes light to be emitted which has an intensity proportional to the ozone concentration. The light intensity is measured with a photomultiplier. The response time of the chemiluminescence reaction is very short, for example 0.1 seconds.

The chemiluminescence technology is used in various ozone sensors.

FIG. 3 shows the design of a known ozone sensor. This sensor, however, is also unsuitable because of its dimensions (length/height/depth) of 180/230/150 mm and because of its weight in an order of magnitude of approximately 800 g.

In the shown ozone sensor, the ozone-containing air to be measured is drawn in with the aid of a fan 34, in the direction of an arrow III, and transported across a chemiluminescence disc 33. The disc 33 reacts with the ozone in the measurement air and emits a light 35 of an intensity proportional to the ozone concentration. The intensity of the emitted light is measured with a photomultiplier 32. Light traps 31 integrated into the airflow channel substantially keep the daylight away from the actual measuring chamber.

Regarding the flow characteristics, it has been found that below a critical speed of the airflow across the chemiluminescence disc, the output signal of the chemical reaction is proportional to the mass of the ozone in the measurement airflow. (See Schurath, U. et al "Principle and Application of a fast sensor for atmospheric ozone", Fresenius, J. Anal. Chem., 340–544–547 of 1991). The resulting output signal, however, is speed-dependent.

Above this critical speed (the minimum speed), the output signal is no longer speed- dependent and only depends on the ozone concentration in the measured air. To be certain that the respective minimum speed is effectively exceeded, the existing sensor systems have been designed with sufficiently large components.

In the existing sensor systems, the dependence of the chemiluminescence reaction on the pressure and humidity has been corrected with correction polynomial equations. The temperature dependence of the existing systems has been bypassed by using a regulated electric heater to maintain the chemiluminescence reaction at a constant temperature. However, these measures have a negative impact on the weight, dimensions and electrical consumption of the sensor and are thus not feasible in a dropsonde.

SUMMARY OF THE INVENTION

Accordingly, the present invention has an object, among others, to overcome deficiencies in the prior art such as noted above, and it is an object of the invention to modify a device known from the prior art for measuring the ozone concentration in air, to obtain a device that can be housed inside a dropsonde and also remains functional without thermostatic control elements.

In accomplishing the foregoing object, there is provided in accordance with the present invention a device for rapidly determining the ozone concentration in air, especially with a sonde.

The device of the invention employs constant recalibration to avoid the need for stabilization. Instead of stabilizing the temperature of the sensing gear, the invention allows the temperature to drift and to affect the output voltage of the photomultiplier tube. However, the photomultiplier output is constantly recalibrated by exposing it continually, at intervals of about one minute, to light from a diode. The light output of the diode is known, so drift due to change in light responsiveness, whether due to temperature or any other reason, can be compensated for.

The temperature is recorded for correcting the ozone reading as a function of the intrinsic output of the chemoluminescence disc. The temperature can also be used to correct for the slight change in the diode's light output with temperature; the diode is provided with a stable voltage, but its temperature is not stabilized.

The diode and the disc are both mounted on a common heat sink, a metal block, so that their temperatures are the same.

Corrections can be made by later correction of transmitted or stored raw data.

The invention includes an air passage, optionally with a fan for boosting air flow through the passage to above the critical speed (at which ozone readings are independent of the air speed), and ambient light blocking by, e.g., a serpentine passageway.

The invention can be thought of as divided into three portions. The first is an airflow passage further comprising: a suction pipe (7) at one end of the passage; a fan (13) at another end of the passage for generating the airflow; a venturi-shaped channel structure (2) along a metal block (9) disposed in the passage between the suction pipe and the fan; and a light trap system (17) for blocking ambient light from the passage.

The second is sensing apparatus further comprising: a temperature sensor (16) mounted in the metal block; a chemiluminescence element (8) attached to a surface of the metal block, a photomultiplier (6) having a window facing the chemiluminescence element, the photomultiplier producing an output voltage in response to light entering the window; and a light-emitting diode (LED 15) integrated in the metal block.

The third is means for switching the light-emitting diode (LED 15) in a predetermined switching cycle wherein the light-emitting diode provides a reference light intensity periodically to the photomultiplier (6), thus periodically overriding an actual ozone measurement signal voltage, whereby temperature dependence of the output voltage of the photomultiplier (6) is periodically recalibrated.

BRIEF DESCRIPTION OF THE DRAWING

The above and other objects and the nature and advantages of the present invention will become more apparent from the following detailed description, based on preferred embodiments of the invention, with reference to the accompanying drawings in which.

DETAILED DESCRIPTION OF THE PREFERRED EMBODIMENT

Figure 1:
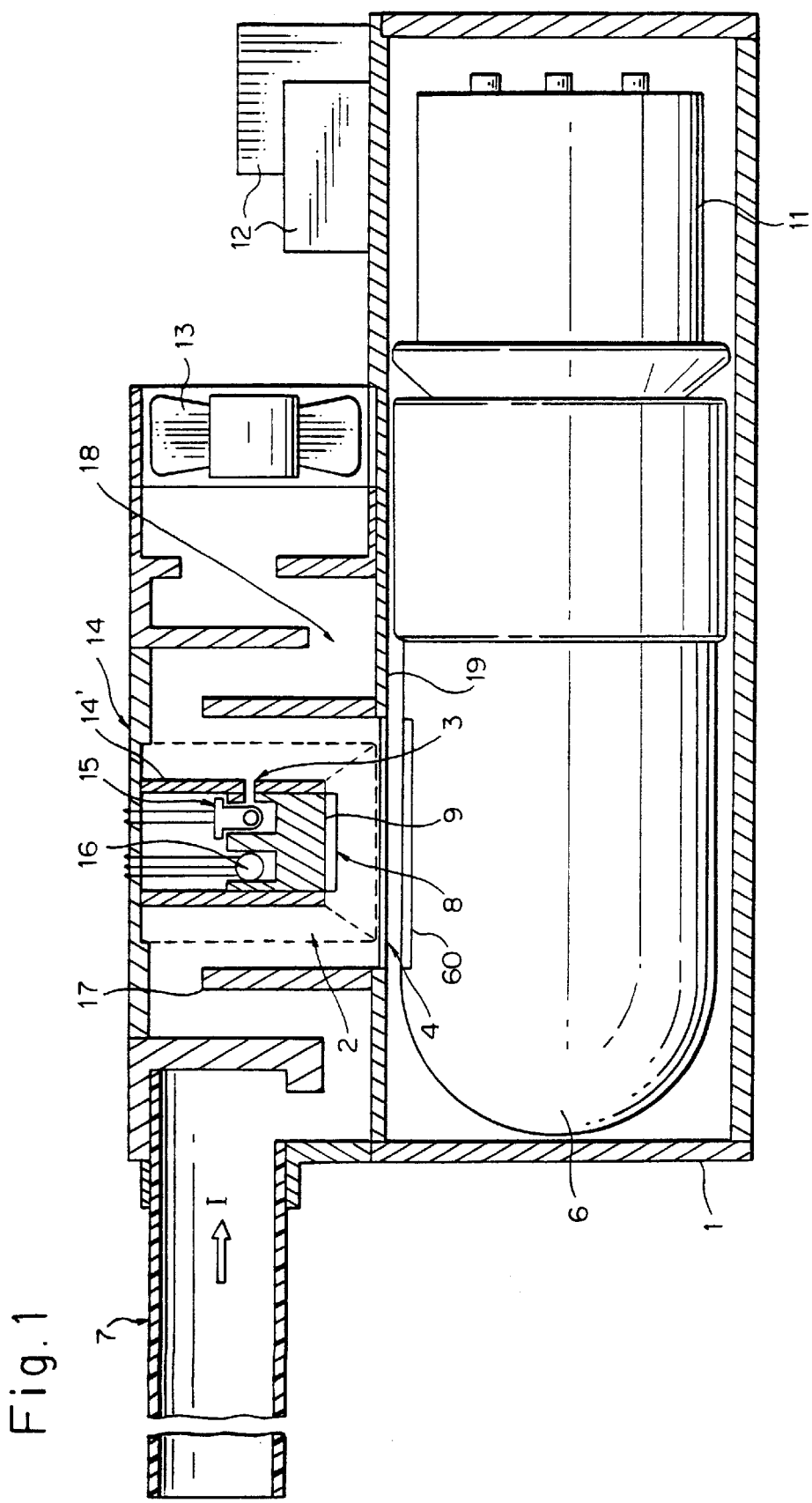
FIG. 1 is a schematic sectional view of a preferred embodiment of the device according to the invention.

FIG. 1 shows, in a sectional view, the integral elements of an ozone sensor which can be housed inside a dropsonde. A sensor casing 1, the lower portion of which is depicted in FIG. 1, which is preferably manufactured from black polyvinyl chloride (PVC), TEFLON, or the like, holds a photomultiplier 6, for example, the Hamamatsu R 931 A with a socket E717.-35 which is illustrated in FIG. 1 on the right.

At the upper left end of the sensor casing 1 shown in FIG. 1, a suction pipe 7 is indicated schematically, which is preferably also made of black Teflon (registered trademark) or from black PVC or similar material. Behind the suction pipe 7, light traps, which are illustrated schematically in the drawing, are installed in the upper portion of the sensor casing 1, whereby said light trap system is designed and implemented in a manner so that the dimensions of the airflow paths along the air measurement path (with the direction of the airflow indicated by an arrow I in the suction pipe) are equal to or larger than the cross-section of the suction pipe 7 which has an interior diameter of 12 mm, for example.

When viewed in the direction of the flow, a metal block 9 installed in-line behind the light trap system 17 is encompassed by a channel structure 2, as indicated by the dashed line in FIG. 1, whereby said channel structure 2 creates a venturi effect. The geometry of the channel structure 2 with its venturi effect is preferably designed with a size ratio of inlet cross-section to outlet cross-section of 2:1. This ensures that a minimum speed of 80 centimeters per second (cm/s) across a chemiluminescence disc 8 attached to the bottom of the metal block 9 is attained, as required for an ozone sensor according to the invention.

Figure 4:
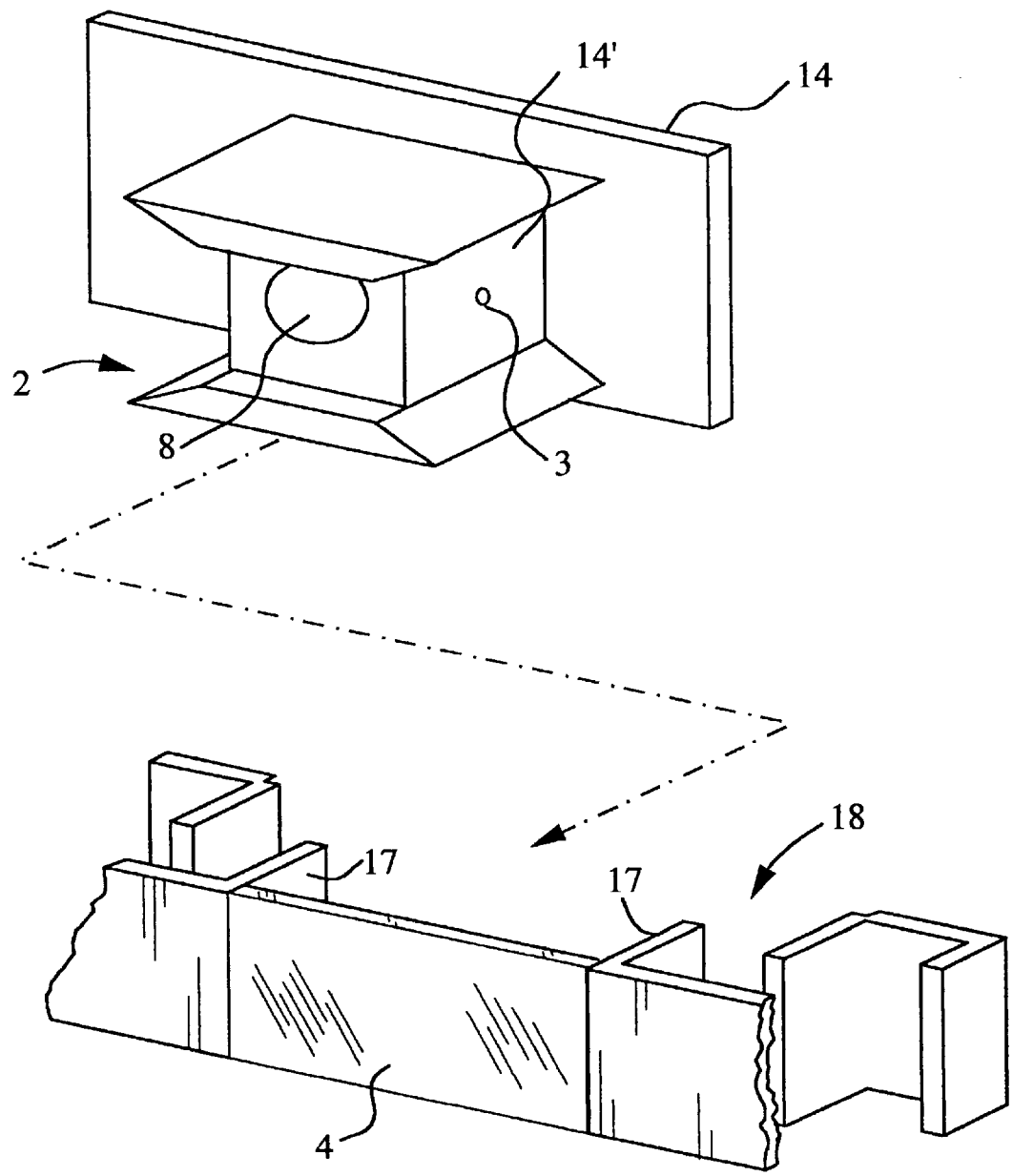
FIG. 4 is an exploded perspective partial cutaway view of the venturi assembly.

The channel structure 2 is more clearly shown in FIG. 4. The truncated pyramidal shape narrows the cross-sectional area across the air flow channel 18 where the disc 8 is located, near the open end of the slot structure including wall 14'. This narrowing speeds the air flow near the disc 8 by the venturi effect.

The upper portion of the metal block 9 facing away from the chemiluminescence disc 8 contains a temperature sensor 16 and a light-emitting diode (LED) 15 serving as a reference light source. On the right side of the LED 15 shown in FIG. 1, a preferably circular exit opening 3 for the light emitted by the LED 15 is formed in the metal block 9 and in the wall 14' located behind the metal block 9 supporting same. The top of the sensor casing 1 is closed with a lid to enclose all the operational parts and the air passage (not shown).

Behind the metal block 9 housed in the venturi-shaped channel structure 2, airflow channel 18—indicated schematically in FIG. 1—is installed in the upper portion of the casing 1 and connected to a fan 13 on its right end shown in FIG. 1. The fan 13 may be for example a Sunol Model 1212 PFB2, which is rated for operation at 12 V but was operated at 16 V in the ozone sensor according to the invention.

The fan has an optimized nozzle geometry, i.e., a design in which the ratio of inlet opening cross-section to exit opening cross-section is approximately 2:1. In an implemented embodiment of the invention, the cross-section of the inlet opening is 110 mm² and the cross-section of the fan outlet opening is 62 mm. This ensures that the required minimum speed of 80 cm/s across the chemiluminescence disc is attained.

At the same time the created nozzle geometry also results in an optimization between a maximum speed attainable with this type of fan and a flow resistance which increases with a smaller nozzle outlet cross-section.

Figure 2:
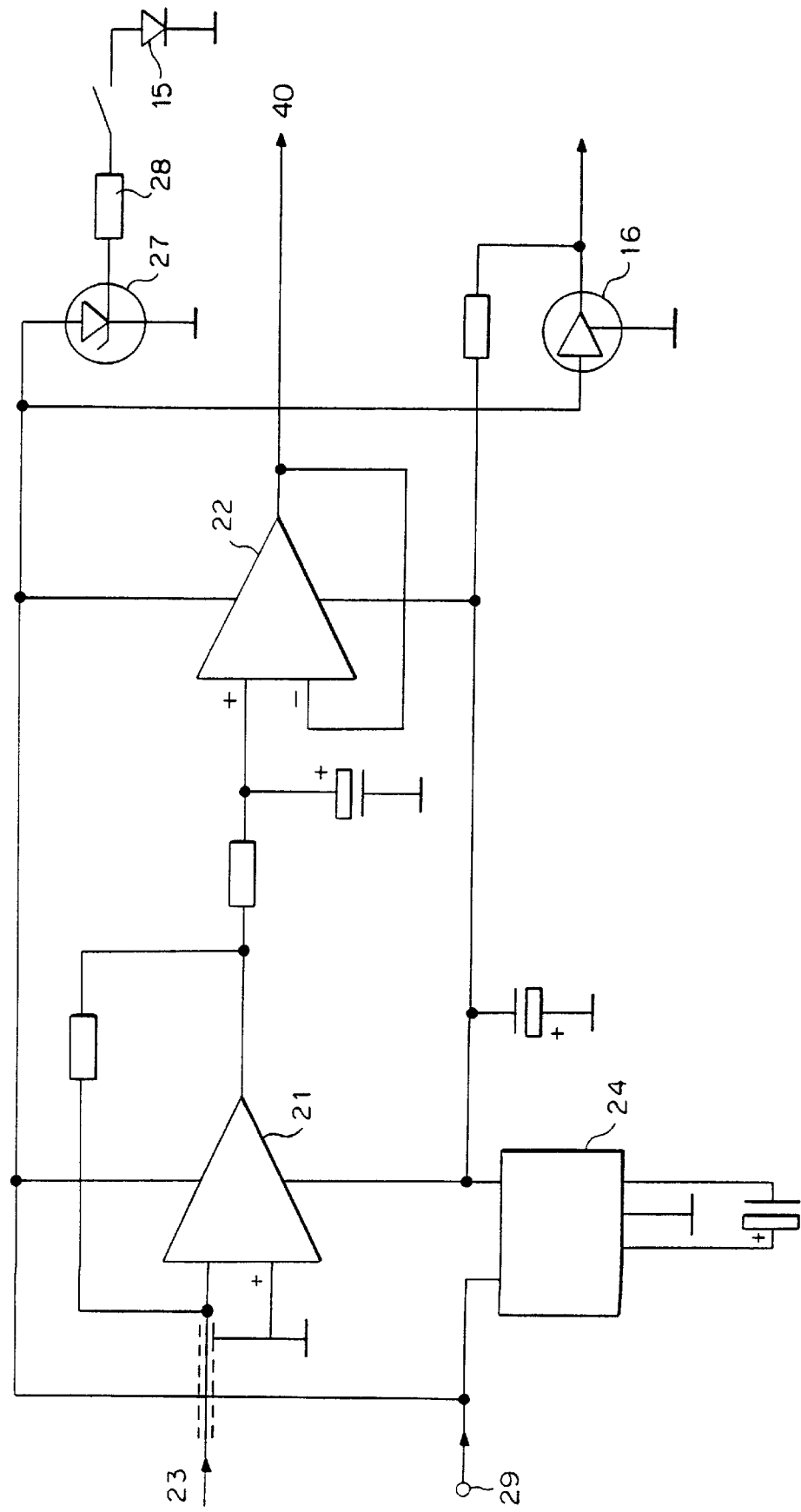
FIG. 2 is a schematic view of signal processing and control circuitry for the device according to the invention.
Figure 3:
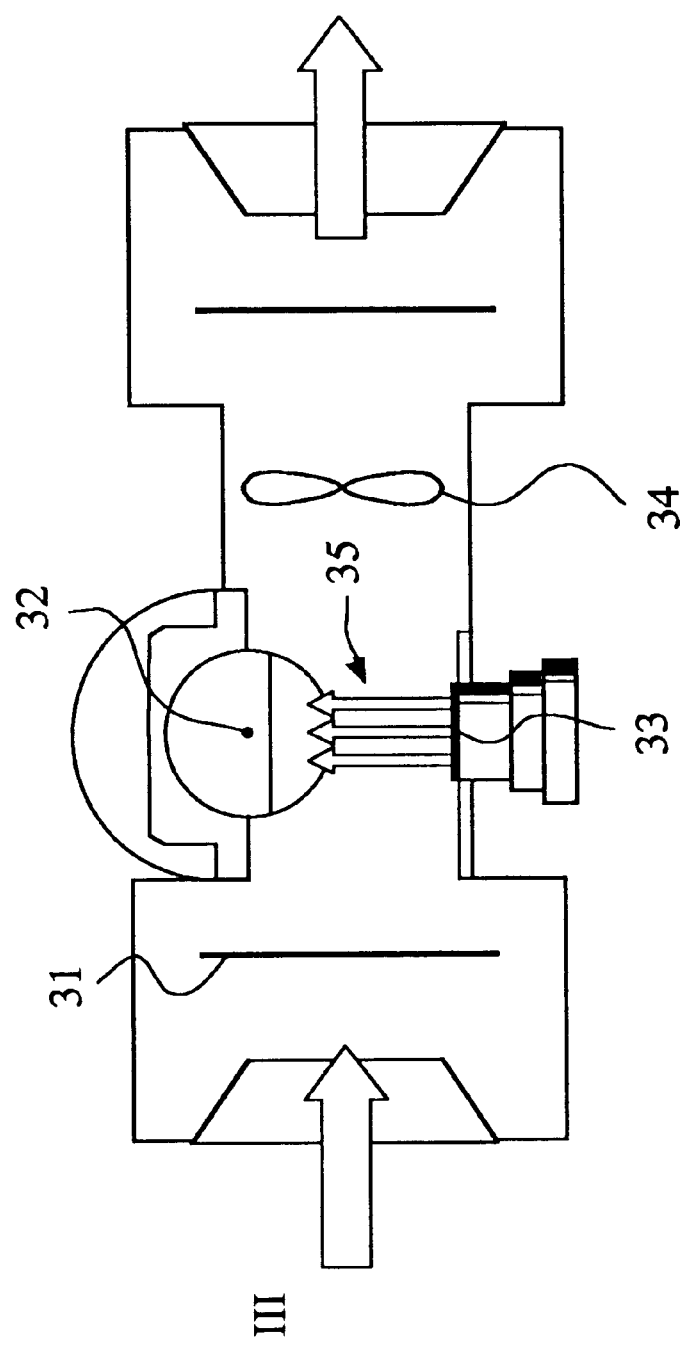
FIG. 3, labeled "prior art", is a schematic section through a known ozone sonde.

FIG. 2 illustrates the integral electronic components of a circuitry for signal processing and monitoring in the preferred embodiment of the device according to the invention for housing inside a dropsonde. The output signal 23 of the photomultiplier tube of the ozone sensor is given to the input of an operation amplifier (OP) 21 with a very high input resistance.

The negative voltage supply for the operation amplifier is generated by means of a voltage converter 24 which is connected with the 12/15 V-battery. The output of the operation amplifier 21 is given to a voltage follower 22 over a RC low pass. At point 40 can be taken off the ozone signal. With a feedback resistor (1 MΩ) across the operation amplifier 21 it can be reached an output level of 5 V at an ozone concentration of 500 ppb.

To stabilize the supply voltage LED 15 a reference unit 27 which generates 2.5 V is used. The LED is taken for temperature correction of the ozone signal. It is thermocoupled with a temperature sensor 16 which provides for an output voltage of 10 mV/°C., so that +25° C. 0.25 V and −25° C. 0.25 V indicate. As the temperature dependency of the LED 15 is known, the light output of the LED 15 is also known. The signal 25 from the PMT due to the ozone-induced chemiluminiscence can then be scaled using this known LED-induced signal. The total power consumption is to be 0.5 Watt at 15 V.

The lower portion of the sensor casing 1, in which the photomultiplier 6 is housed, is separated by a partitioning wall 19 from the portion of the casing containing, for example, the metal block 9. In the partitioning wall 19, a glass pane 4 is installed below the chemiluminescence disc 8 attached to the bottom of the metal block 9. Adjacent the glass pane 4, across from the chemiluminescence disc 8, the entrance window 60 of the photomultiplier 6 is placed.

The very small space requirement and low overall weight of the device according to the invention for determining the ozone concentration in air, coupled with its comparatively very low energy consumption, makes it possible to house the device according to the invention inside a dropsonde.

As with the existing ozone sensors currently used in the chemiluminescence technology, a measurement sensitivity ED under standard conditions, i.e., at a pressure of 1013 hPA (1013 hundred pascals) and a temperature of 20° C., must also be determined for the device according to the present invention designed for the installation and use in a dropsonde. To determine said measurement sensitivity $\epsilon_o$, air with varying ozone mixing ratios is transported through the ozone sensor in separate batches, and the respective output voltages of the photomultiplier 6 are measured. The measurement sensitivity $\epsilon_o$ under standard conditions can thus be determined as follows:

$$\epsilon_0 = \frac{\text{Output voltage}}{\text{Ozone mixing ratio}} \tag{1}$$

The light intensity of the chemiluminescence reaction at the chemiluminescence disc 8 and the resulting output voltage or measurement sensitivity of the photomultiplier 6, respectively, are temperature-dependent. In the existing ozone sensors (see the explanations by Schurath et al) the carrier plate has been thermostatically regulated to 30° C. and the entire system thermally insulated from the ambient air with insulating materials. Since this solution could not be adopted for an ozone sensor to be operated in connection with a dropsonde, primarily for weight reasons and because of the amount of electrical energy required by the existing ozone sondes, an additional temperature calibration was created for the device according to the invention. For the temperature calibration, an ozone sensor of the design described based on FIG. 1 was placed inside a so-called environmental chamber whereby both the temperature of the environmental chamber as well as the temperature of the measurement air transported through the ozone sensor could be varied between −70° C. and 40° C. The temperature dependence of the measurement sensitivity $\epsilon$, which is now known, can then be determined for a predetermined ozone mixing ratio based on the following correlation:

$$\epsilon(T) = \epsilon_o(AT+B) \tag{2}$$

This requires determining of the coefficients A and B. If the above-described laboratory calibration according to equation (2) is used, the respective measurement sensitivity can be determined during a subsequent measurement performed with the ozone sonde at a known temperature of the metal block 9, to which the chemiluminescence disc 8 is attached. The result may then be used to determine, based on the measured output voltage of the photomultiplier 6, with the aid of equation (1), the required ozone mixing ratio.

The above described process does not take into consideration the fact, however, that the specifically selected and implemented design of the photomultiplier 6, and accordingly also its output voltage, are temperature-dependent as well. To take this fact into account, and specifically to correct this effect and keep it to a minimum, the electronic design was dimensioned so that a high-voltage supply of 750 V, instead of the nominally required 1200 V, is sufficient for the photomultiplier 6 to maintain a sufficient output signal.

In this context it is advantageous that the photomultiplier 6 is considerably less temperature sensitive at the relatively low supply voltage of 750 V. Furthermore, at such relatively low temperatures disturbances of other dropsonde sensors and the telemetry, caused by an interference with the high voltage, are considerably reduced as well. Also, because of the design of the ozone sensor according to the invention, any temperature variation remaining at the photomultiplier is corrected anyhow.

As shown in FIG. 1, the light-emitting diode (LED) 15, which only requires a low voltage supply, is integrated into the metal block 9. This means that the LED 15 is in thermal balance with the metal block 9. Furthermore, the temperature dependence of the light intensity of the LED 15 is a known factor.

When the LED 15 is in operation, its light can thus exit through the opening 3 provided for this purpose on the side of the block (see FIG. 1), whereby the diameter of the light opening is preferably 1 mm, and the light intensity can be received by the photomultiplier.

If, in the course of an ozone measurement performed with a dropsonde which is equipped with the device according to the invention, the LED 15 is operated with a known light intensity and a switching cycle of 1 second per minute at varying measurement air temperatures, the temperature dependence of the photomultiplier system can be corrected retroactively based on the radiotelemetrically transmitted measurement data.

The pressure and humidity dependence of the chemical reaction, or of the emitted light intensity, respectively, is corrected in a similar manner, as described by Schurath et al.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means and materials for carrying out various disclosed functions may take a variety of alternative forms without departing from the invention.

Thus the expressions "means to . . ." and "means for . . ." as may be found in the specification above and/or in the claims below, followed by a functional statement, are intended to define and cover whatever structural, physical, chemical or electrical element or structure may now or in the future exist carries out the recited function, whether or not precisely equivalent to the embodiment or embodiments disclosed in the specification above; and it is intended that such expressions be given their broadest interpretation.

What is claimed is:

1. A device for determining ozone concentration in air by utilizing the surface chemiluminescence effect, comprising:
   an airflow passage further comprising: a suction pipe (7) at one end of the passage; a fan (13) at another end of the passage for generating the airflow; a venturi-shaped channel structure (2) along a metal block (9) disposed in the passage between the suction pipe and the fan; and a light trap system (17) for blocking ambient light from the passage;
   sensing apparatus further comprising: a temperature sensor (16) mounted in the metal block; a chemiluminescence element (8) attached to a surface of the metal block, a photomultiplier (6) having a window facing the chemiluminescence element, the photomultiplier producing an output voltage in response to light entering the window; and a light-emitting diode (LED 15) integrated in the metal block; and
   means for switching the light-emitting diode (LED 15) in a predetermined switching cycle wherein the light-emitting diode provides a reference light intensity periodically to the photomultiplier (6), thus periodically overriding an actual ozone measurement signal voltage, whereby temperature dependence of the output voltage of the photomultiplier (6) is periodically recalibrated.

2. The device according to claim 1, wherein the venturi-shaped channel structure (2) includes an entrance cross-section dimensioned in proportion to an exit cross-section such that a minimum measurement airflow is attained past the chemiluminescence element.

3. The device according to claim 2, wherein the minimum 80 cm/s.

4. The device according to claim 1, wherein the suction pipe (7) includes an entrance cross-section, the fan (13) includes an exit cross-section, and the entrance cross-section is dimensioned in proportion to the exit cross-section such that a minimum measurement airflow is attained past the chemiluminescence element.

5. The device according to claim 4, wherein the minimum 80 cm/s.

6. The device according to claim 1, further comprising calibration means for calibrating the device according to a temperature dependence of reactivity of the chemiluminescence element (8) by determining an output voltage of the photomultiplier (6) at a predetermined air ozone concentration as a function of air temperature.

7. The device according to claim 1, wherein the chemiluminescence element comprises a chemiluminescence disc.

8. The device according to claim 1, wherein the light-emitting diode provides the reference light intensity periodically to the photomultiplier (6) through an opening (3) in the metal block.

9. The device according to claim 1, wherein components of the device are housed inside wall areas of a casing (1) and the wall areas, that are exposed to the ozone-containing measurement airflow, includes an ozone-resistant material.

10. The device according to claim 1, wherein the ozone-resistant material includes at least one of TEFLON and polyvinyl chloride (PVC).

11. A dropsonde comprising a device for determining ozone concentration in air by utilizing the surface chemiluminescence effect; the device comprising:
    an airflow passage further comprising: a suction pipe (7) at one end of the passage; a fan (13) at another end of the passage for generating the airflow; a venturi-shaped channel structure (2) along a metal block (9) disposed in the passage between the suction pipe and the fan; and a light trap system (17) for blocking ambient light from the passage;
    sensing apparatus further comprising: a temperature sensor (16) mounted in the metal block; a chemiluminescence element (8) attached to a surface of the metal block, a photomultiplier (6) having a window facing the chemiluminescence element, the photomultiplier producing an output voltage in response to light entering the window; and a light-emitting diode (LED 15) integrated in the metal block; and
    means for switching the light-emitting diode (LED 15) in a predetermined switching cycle wherein the light-emitting diode provides a reference light intensity periodically to the photomultiplier (6), thus periodically overriding an actual ozone measurement signal voltage, whereby temperature dependence of the output voltage of the photomultiplier (6) is periodically recalibrated.

12. The device according to claim 11, wherein the Venturi-shaped channel structure (2) includes an entrance cross-section dimensioned in proportion to an exit cross-section such that a minimum measurement airflow is attained past the chemiluminescence element.

13. The device according to claim 12, wherein the minimum 80 cm/s.

14. The device according to claim 11, wherein the suction pipe (7) includes an entrance cross-section, the fan (13) includes an exit cross-section, and the entrance cross-section is dimensioned in proportion to the exit cross-section such that a minimum measurement airflow is attained past the chemiluminescence element.

15. The device according to claim 14, wherein the minimum 80 cm/s.

16. The device according to claim 11, further comprising calibration means for calibrating the device according to a temperature dependence of reactivity of the chemiluminescence element (8) by determining an output voltage of the photomultiplier (6) at a predetermined air ozone concentration as a function of air temperature.

17. The device according to claim 11, wherein the chemiluminescence element comprises a chemiluminescence disc.

18. The device according to claim 11, wherein the light-emitting diode provides the reference light intensity periodically to the photomultiplier (6) through an opening (3) in the metal block.

19. The device according to claim 11, wherein components of the device are housed inside wall areas of a casing (1) and the wall areas, that are exposed to the ozone-containing measurement airflow, includes an ozone-resistant material.

20. The device according to claim 11, wherein the ozoneresistant material includes at least one of TEFLON and polyvinyl chloride (PVC).

* * * * *